US012611333B2

(12) United States Patent
Li

(10) Patent No.: US 12,611,333 B2
(45) Date of Patent: Apr. 28, 2026

(54) AURILAVE AND VISUAL AURILAVE

(71) Applicant: Wenming Li, Shaoyang (CN)

(72) Inventor: Wenming Li, Shaoyang (CN)

( * ) Notice: Subject to any disclaimer, the term of this patent is extended or adjusted under 35 U.S.C. 154(b) by 700 days.

(21) Appl. No.: 18/078,126

(22) Filed: Dec. 9, 2022

(65) Prior Publication Data

US 2023/0107151 A1 Apr. 6, 2023

(51) Int. Cl.
*A61F 11/00* (2022.01)
*A61B 1/227* (2006.01)
*A61B 1/04* (2006.01)

(52) U.S. Cl.
CPC ............ *A61F 11/006* (2013.01); *A61B 1/227* (2013.01); *A61B 1/04* (2013.01)

(58) Field of Classification Search
CPC ........... A61B 1/227; A61B 1/04; A61B 1/005; A61B 1/015; A61B 1/06; A61B 1/126; A61B 1/00032; A61F 11/006
See application file for complete search history.

(56) References Cited

U.S. PATENT DOCUMENTS 4,760,838 A * 8/1988 Fukuda .................. A61B 1/126
600/158
5,527,275 A * 6/1996 Ginsberg ............ A61M 3/0216
604/38
2003/0187469 A1 10/2003 Olson
2008/0183125 A1 * 7/2008 Issa ....................... A61F 11/006
606/162

2011/0015489 A1 * 1/2011 Raghuprasad ......... A61B 1/227
600/187
2012/0059224 A1 * 3/2012 Wellen ................... A61B 1/227
600/200
2012/0327426 A1 * 12/2012 Hart ...................... A61B 5/1079
356/601
2016/0279321 A1 * 9/2016 Bansal ................ A61M 3/0202
2019/0159936 A1 5/2019 Olson
2020/0268556 A1 8/2020 Siljkovic

FOREIGN PATENT DOCUMENTS

CN 211834820 U * 11/2020 ............... A61B 1/24
DE 112011105458 T5 * 4/2014 ......... A61B 1/00108

OTHER PUBLICATIONS

CN-211834820-U, English language machine translation (Year: 2020).*
DE-112011105458-T5, English language machine translation (Year: 2014).*

* cited by examiner

*Primary Examiner* — Wesley G Harris
(74) *Attorney, Agent, or Firm* — Hemisphere Law, PLLC

(57) ABSTRACT

The present invention discloses an aurilave, including: a water storage tank provided with a mounting port; a housing detachably arranged on the mounting port of the water storage tank; and an ear-washing assembly including a control plate arranged in the housing, a water-pumping motor arranged in the housing and electrically connected to the control plate, a water inlet pipe connected to a water inlet port of the water-pumping motor at one end thereof, a water outlet pipe connected to a water outlet port of the water-pumping motor at one end thereof, a nozzle arranged on the water outlet port of the water outlet pipe, and a transparent water baffle arranged on the water outlet pipe.

15 Claims, 6 Drawing Sheets

AURILAVE AND VISUAL AURILAVE

TECHNICAL FIELD

The present invention relates to the technical field of an ear-cleaning apparatus, and particularly to an aurilave and a visual aurilave.

BACKGROUND

In people's daily ear-canal cleaning, forceps, an ear spoon and other hard objects are commonly used for cleaning an ear canal. Since a user cannot see a situation in the ear canal during self-cleaning of the ear canal, and it is difficult to control a force during use, it is easy to damage an ear membrane or the ear canal during the ear-canal cleaning, which leads to an ear disease. A safety risk exists in a method for cleaning the ear canal in the prior art.

SUMMARY

A main objective of the present invention is to propose an aurilave, which is intended to improve safety of ear cleaning.

To achieve the above objective, the aurilave proposed according to the present invention includes:

a water storage tank provided with a mounting port;

a housing detachably arranged on the mounting port of the water storage tank; and, an ear-washing assembly including a control plate arranged in the housing, a water-pumping motor arranged in the housing and electrically connected to the control plate, a water inlet pipe connected to a water inlet of the water-pumping motor at one end thereof, a water outlet pipe connected to a water outlet of the water-pumping motor at one end thereof, a nozzle arranged on the other end of the water outlet pipe, and a transparent water baffle arranged on the water outlet pipe, the other end of the water inlet pipe extending into the water storage tank.

Optionally, the ear-washing assembly includes a sprinkler seat. One end of the sprinkler seat is fixed in the housing and communicated with the water outlet pipe, and the other end of the sprinkler seat protrudes out of the housing. The nozzle is arranged at one end of the sprinkler seat located outside the housing.

Optionally, the ear-washing assembly further includes a front cover arranged on the housing and an LED lamp plate arranged within the front cover and emitting light in a direction toward the nozzle. A middle of the front cover is opened and provided with a fixing hole for fixing the sprinkler seat. The front cover is opened and provided with a light-transmitting hole for accommodating lamp beads of the LED lamp plate.

Optionally, the front cover is formed with a sealing groove relative to the other side of the LED lamp plate. The light-transmitting hole is located at a bottom of the sealing groove. The aurilave further includes a transparent sealing ring arranged within the sealing groove.

Optionally, the transparent water baffle is in a form of a disk raised in a middle thereof.

Optionally, the ear-washing assembly further includes a rear cover and a power switch arranged on the rear cover, and the power switch is electrically connected to the control plate.

Optionally, the ear-washing assembly further includes a key switch arranged on the housing for controlling the water-pumping motor.

Optionally, the housing is L-shaped.

Optionally, the ear-washing assembly further includes a battery. The battery is arranged within the housing and electrically connected to the control plate.

Optionally, the ear-washing assembly further includes a gravity ball. The gravity ball is arranged at one end of the water inlet pipe extending into the water storage tank.

The present invention also proposes a visual aurilave, including:

a water storage tank provided with a mounting port;

a housing detachably arranged on the mounting port of the water storage tank;

an ear-washing assembly including a control plate arranged in the housing, a water-pumping motor arranged in the housing and electrically connected to the control plate, a water inlet pipe connected to a water inlet of the water-pumping motor at one end thereof, a water outlet pipe connected to a water outlet of the water-pumping motor at one end thereof, a nozzle arranged on the other end of the water outlet pipe, and a transparent water baffle arranged on the water outlet pipe, the other end of the water inlet pipe extending into the water storage tank; and a camera assembly including a camera arranged on the ear-washing assembly and a signal-transmitting module arranged on the control plate. The camera is electrically connected to the control plate and arranged close to the nozzle. The signal-transmitting module is configured to transmit video signals captured by the camera to a display apparatus.

Optionally, the ear-washing assembly includes a sprinkler seat. One end of the sprinkler seat is fixed in the housing and communicated with the water outlet pipe, and the other end of the sprinkler seat projects out of the housing. The nozzle is arranged at one end of the sprinkler seat located outside the housing.

Optionally, the sprinkler seat is opened and provided with a mounting channel. The camera is arranged in the mounting channel.

Optionally, the camera module includes the camera and a plurality of LED lamp beads provided on the camera and arranged in a circular shape.

Optionally, the ear-washing assembly further includes a front cover arranged on the housing and an LED lamp plate arranged within the front cover and emitting light in a direction toward the nozzle. A middle of the front cover is opened and provided with a fixing hole for fixing the sprinkler seat. The front cover is opened and provided with a light-transmitting hole for accommodating the lamp beads of the LED lamp plate.

The front cover is formed with a sealing groove relative to the other side of the LED lamp plate. The light-transmitting hole is located at a bottom of the sealing groove. The aurilave further includes a transparent sealing ring arranged within the sealing groove.

Optionally, the transparent water baffle is in a form of a disk raised in a middle thereof.

Optionally, the ear-washing assembly further includes a rear cover and a power switch arranged on the rear cover. The power switch is electrically connected to the control plate.

Optionally, the ear-washing assembly further includes a key switch arranged on the housing for controlling the water-pumping motor.

Optionally, the housing is L-shaped.

Optionally, the ear-washing assembly further includes a gravity ball. The gravity ball is arranged at one end of the water inlet pipe extending into the water storage tank.

The aurilave according to the technical solution of the present invention includes the water storage tank, the housing, and the ear-washing assembly. The water storage tank is configured to store a cleaning liquid. The housing is detachably arranged on the mounting port of the water storage tank. The ear-washing assembly is arranged in the housing. The control plate is configured to control the water-pumping motor. The water-pumping motor has the water inlet port and the water outlet port. One end of the water inlet pipe is connected to the water inlet port of the water-pumping motor, and the other end of the water inlet pipe extends into the water storage tank. One end of the water outlet pipe is connected to the water outlet port of the water-pumping motor, and the other end of the water outlet pipe extends out of the housing. The nozzle is arranged at one end of the water outlet pipe extending out of the housing. The transparent water baffle is sleeved on the water outlet pipe near the nozzle. The water-pumping motor pumps the cleaning liquid in the water storage tank and sprays the cleaning liquid via the water outlet pipe to clean an inner side of an ear, which effectively prevents damage to the ear canal and improves safety of ear-canal cleaning.

BRIEF DESCRIPTION OF THE DRAWINGS

In order to explain embodiments of the present invention or the technical solutions in the prior art more clearly, the following briefly introduces the drawings that need to be used in the embodiments or the prior art. Obviously, the drawings in the following description are only some of embodiments of the present invention. Those skilled in the art may obtain other drawings based on structures shown in these drawings without creative labor.

Figure 1:
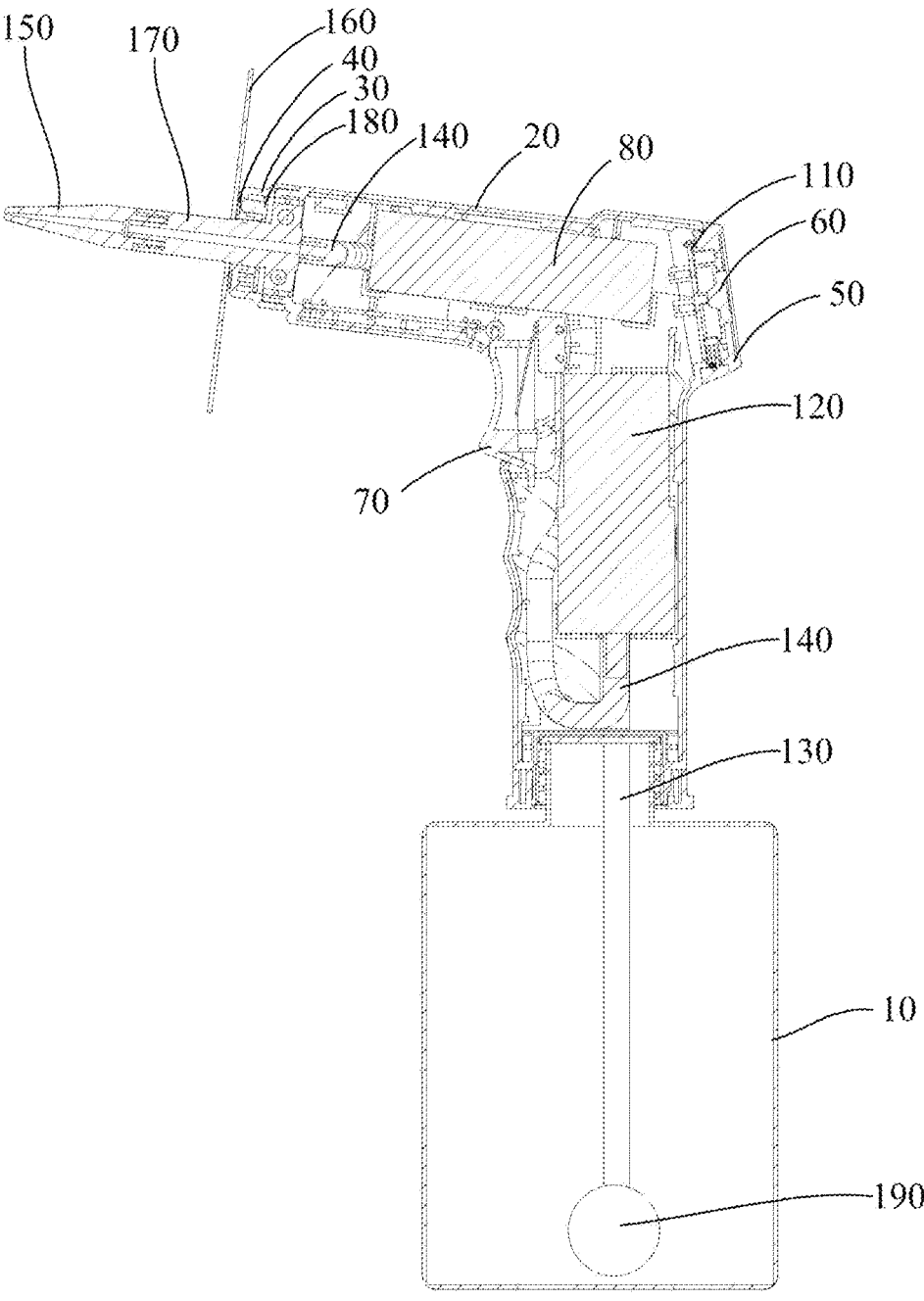
FIG. 1 is a cross-sectional schematic diagram of an aurilave according to the present invention.

The description of reference signs:

| Reference signs | Name (s) |
| --- | --- |
| 10 | Water storage tank |
| 20 | Housing |
| 30 | Front cover |
| 31 | Sealing groove |
| 32 | Fixing hole |
| 33 | Light-transmitting hole |
| 40 | Transparent sealing ring |
| 50 | Rear cover |
| 60 | Power switch |
| 70 | Key switch |
| 80 | Battery |
| 90 | Camera assembly |
| 91 | Camera |
| 92 | LED lamp beads |

-continued

| Reference signs | Name (s) |
| --- | --- |
| 110 | Control plate |
| 120 | Water-pumping motor |
| 130 | Water inlet pipe |
| 140 | Water outlet pipe |
| 150 | Nozzle |
| 160 | Transparent water baffle |
| 170 | Sprinkler seat |
| 171 | Mounting channel |
| 172 | Water guiding channel |
| 180 | LED lamp plate |
| 190 | Gravity ball |

The realization, functional features, and advantages of the present invention will be described further with reference to the drawings.

DETAILED DESCRIPTION OF EMBODIMENTS

The following clearly and completely describes the technical solutions in embodiments of the present invention in conjunction with the drawings in the embodiments of the present invention. Obviously, the described embodiments are only a part of the embodiments of the present invention, rather than all embodiments. Based on the embodiments of the present invention, all other embodiments obtained by those skilled in the art without creative labor shall fall within the protection scope of the present invention.

It should be noted that if the embodiments of the present invention involve directional indications (such as up, down, left, right, front, back . . . ), the directional indications are only used to explain a relative position relationship and movement among various components under a certain posture (as shown in the drawings). If a specific posture changes, the directional indication also changes accordingly.

In addition, if there are descriptions of terms such as "first", "second" and the like in the embodiments of the present invention, the descriptions of the terms such as "first", "second" and the like are merely intended for a purpose of description, and shall not be understood as an indication or implication of relative importance or implicit indication of a quantity of indicated technical features. Therefore, the features defined with "first" and "second" may explicitly or implicitly include at least one of the features. In addition, the meaning of "and/or" in the whole text is to include three parallel schemes. Taking "A and/or B" as an example, "A and/or B" includes scheme A, or scheme B, or a scheme that A and B are satisfied at the same time. In addition, the technical solutions of various embodiments can be combined with each other, but should be based on what can be achieved by those skilled in the art. When a combination of technical solutions is contradictory or cannot be achieved, it should be considered that such a combination of technical solutions does not exist, and also does not fall within the scope of protection required by the present invention.

The present invention proposes an aurilave.

In an embodiment of the present invention, as shown in FIGS. 1 to 5, the aurilave includes:

a water storage tank 10 provided with a mounting port;

a housing 20 detachably arranged on the mounting port of the water storage tank 10; and an ear-washing assembly including a control plate 110 arranged in the housing 20, a water-pumping motor 120 arranged in the housing 20 and electrically connected to the control plate 110, a water inlet pipe 130 connected to a water inlet port of the water-pumping motor 120 at one end thereof, a water outlet pipe 140 connected to a water outlet port of the water-pumping motor 120 at one end thereof, a nozzle 150 arranged on the other end of the water outlet pipe 140, and a transparent water baffle 160 arranged on the water outlet pipe 140. The other end of the water inlet pipe extends into the water storage tank.

In this embodiment, the water storage tank 10 is configured to store a cleaning liquid. A body of the water storage tank is opened and provided with a mounting port for mounting the housing 20 and for storing and discharging the cleaning liquid.

The housing 20 is the housing 20 of a hand-held portion of the aurilave, and configured to provide a mounting position for the ear-washing assembly. The housing 20 can be detachably arranged on the mounting port of the water storage tank 10. It can be understood that the housing 20 can be threadedly connected to the water storage tank 10, and can also be snap-fastened to the water storage tank 10. Specifically, no limitation is provided herein. Additionally, the housing 20 may be mounted on a top of the water storage tank 10, at a side wall of the water storage tank 10 or at a bottom of the water storage tank 10. Specifically, no limitation is provided herein. Preferably, the housing 20 is mounted on the top of the water storage tank 10 and threadedly connected to the water storage tank 10. Specifically, a bottom end of the housing 10 is provided with internal threads. The top of the water storage tank 10 protrudes and is provided with a threaded boss. The housing 20 is threadedly connected to the threaded boss so that the housing 20 and the water storage tank 10 are relatively fixed. It needs to be explained that an opening of the water storage tank 10 is located on a top of the threaded boss so that the housing 20 and the water storage tank 10 are communicated with each other.

The ear-washing assembly is a power transmission device of the aurilave, and is configured to apply a driving force to the cleaning liquid in the water storage tank 10 and discharge the cleaning liquid, thereby achieving an effect of flushing an ear canal. Specifically, the control plate 110 is arranged in the housing 20 and configured to be connected to a power source and control the water-pumping motor 120. The water-pumping motor 120 has the water inlet port and the water outlet port. One end of the water inlet pipe 130 is connected to the water inlet port of the water-pumping motor 120, and the other end of the water inlet pipe extends from the mounting port of the water storage tank 10 into the water storage tank 10 so that the water-pumping motor 120 pumps the cleaning liquid in the water storage tank 10. One end of the water outlet pipe 140 is connected to the water outlet port of the water-pumping motor 120, and the other end of the water outlet pipe extends out of the housing 20 and is configured to spray the cleaning liquid. The water outlet end of the water outlet pipe 140 is provided with a nozzle 150. The nozzle 150 is configured to reduce an aperture of the water outlet pipe 140 to improve a water pressure strength. In addition, the transparent water baffle 160 is sleeved on the water outlet pipe 140 close to the nozzle 150. The transparent water baffle 160 is configured to fend against water drops splashed from the ear so that the user can conveniently observe a cleaning condition within the ear canal.

The aurilave according to the technical solution of the present invention includes the water storage tank 10, the housing 20, and the ear-washing assembly. The water storage tank 10 is configured to store the cleaning liquid. The housing 20 is detachably arranged on the mounting port of the water storage tank 10. The ear-washing assembly is arranged in the housing 20. The control plate 110 is configured to control the water-pumping motor 120. The water-pumping motor 120 has the water inlet port and the water outlet port. One end of the water inlet pipe 130 is connected to the water inlet port of the water-pumping motor 120, and the other end of the water inlet pipe 130 extends into the water storage tank 10. One end of the water outlet pipe 140 is connected to the water outlet port of the water-pumping motor 120, and the other end of the water outlet pipe extends out of the housing 20. The nozzle 150 is arranged at one end of the water outlet pipe 140 extending out of the housing 20. The transparent water baffle 160 is sleeved on the water outlet pipe 140 near the nozzle 150. The water-pumping motor 120 pumps the cleaning liquid in the water storage tank 10 and sprays the cleaning liquid via the water outlet pipe 140 to clean an inner side of an ear, which effectively prevents damage to the ear canal and improves safety of ear-canal cleaning.

Further, as shown in FIGS. 1 to 5, the ear-washing assembly includes a sprinkler seat 170. One end of the sprinkler seat 170 is fixed in the housing 20 and communicated with the water outlet pipe 140, and the other end of the sprinkler seat 170 protrudes out of the housing 20. The nozzle 150 is arranged at one end of the sprinkler seat 170 located outside the housing 20. In this embodiment, the sprinkler seat 170 is made of a rigid material. An inner part of the sprinkler seat is formed with a water guiding channel 172. One end of the sprinkler seat 170 is fixed in the housing 20. One end of the water outlet pipe 140 is fixed on the sprinkler seat 170 and communicated with the water guiding channel 172 of the sprinkler seat 170. The other end of the sprinkler seat 170 extends out of the housing 20 and is configured to spray water. The nozzle 150 is arranged at one end of the sprinkler seat 170 extending out of the housing 20. Arrangement of the sprinkler seat 170 makes a water outlet end of the aurilave form a stable water flow direction, thus effectively improving water flow stability of the aurilave, and improving practicality of the aurilave.

Figure 2:
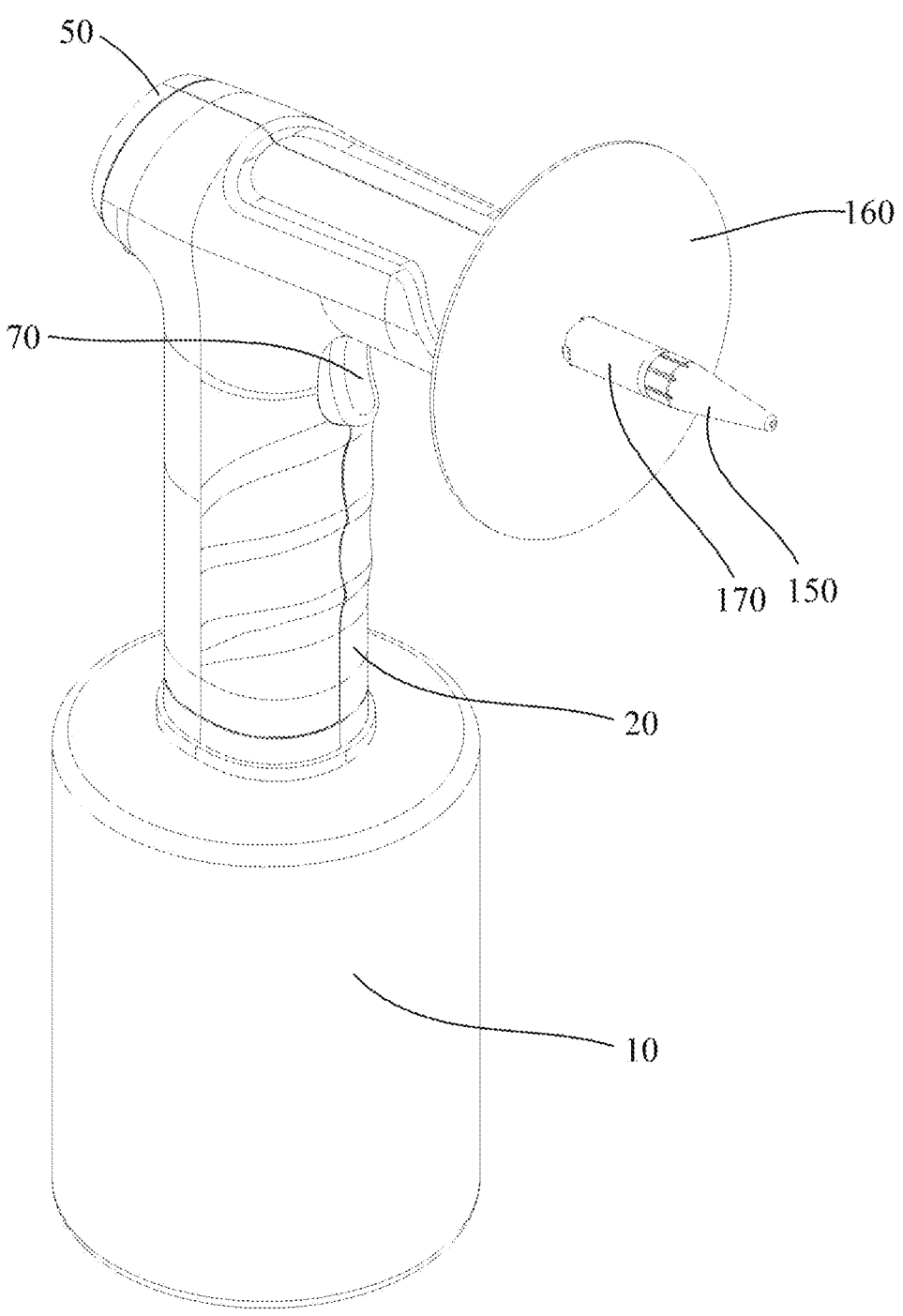
FIG. 2 is a schematic structural diagram of an aurilave according to the present invention.

Further, as shown in FIGS. 1 to 2, the ear-washing assembly further includes a front cover 30 arranged on the housing 20 and an LED lamp plate 180 arranged within the front cover 30 and emitting light in a direction toward the nozzle 150. A middle of the front cover 30 is opened and provided with a fixing hole 32 for fixing the sprinkler seat 170. The front cover 30 is opened and provided with a light-transmitting hole 33 for accommodating lamp beads of the LED lamp plate 180. In this embodiment, the housing 20 includes a left housing and a right housing. The left housing and the right housing are snap-fitted to form a mounting space of the ear-washing assembly. The front cover 30 is arranged at a water outlet end of the housing 20 to improve structural stability of the left housing and the right housing. The LED lamp plate 180 is configured to improve brightness in the ear canal and facilitate the user to understand a cleaning situation in the ear canal. Specifically, a middle of the front cover 30 is opened and provided with a fixing hole 32 for fixing the sprinkler seat 170 to improve mounting stability of the sprinkler seat 170. Additionally, the front cover 30 is also opened and provided with the light-transmitting hole 33 for accommodating the lamp beads of the LED lamp plate 180 around an axial direction of the fixing hole 32. The lamp beads are located in the light-transmitting hole 33 and emit light in a direction of the nozzle 150 to illuminate the ear canal, so that the user can more clearly observe a situation in the ear canal. Therefore, the user conveniently cleans the ear canal, thereby effectively improving the practicality of the aurilave.

In addition, a waterproof adhesive ring is also arranged in the fixing hole 32. The waterproof adhesive ring is sleeved on the sprinkler seat 170 and abuts against an inner wall of the fixing hole 32, thereby effectively improving sealing of the aurilave.

Further, the front cover 30 is formed with a sealing groove 31 relative to the other side of the LED lamp plate 180 corresponding to the lamp beads of the LED lamp plate 180. The light-transmitting hole is located at a bottom of the sealing groove 31. A transparent sealing ring 40 is arranged in the sealing groove 31, thereby effectively improving the sealing of the aurilave without affecting a lighting effect of the LED lamp plate 180.

Further, as shown in FIGS. 1 to 5, the transparent water baffle 160 is in a form of a disk raised in a middle thereof. In this embodiment, a middle of the transparent water baffle 160 is raised to achieve a magnifying effect similar to that of a convex lens, thereby facilitating the user to know the cleaning situation within the ear canal. The transparent water baffle 160 is arranged in a disk shape, so that when water drops are splashed on the transparent water baffle 160, the water drops are converged towards a lower middle part of the transparent water baffle 160, thereby reducing coagulation of the water drops on the transparent water baffle 160 to affect the user's viewing. This effectively improves the practicality of the aurilave.

Further, as shown in FIGS. 1 to 5, the ear-washing assembly further includes a rear cover 50 and a power switch 60 arranged on the rear cover 50. The power switch 60 is electrically connected to the control plate 110. In this embodiment, the rear cover 50 is configured to improve structural stability of the housing 20 and provide a mounting position for the power switch 60. The power switch 60 is arranged on the rear cover 50 and electrically connected to the control plate 110 to control a power on/off of the water-pumping motor 120.

Further, as shown in FIGS. 1 to 5, the ear-washing assembly further includes a key switch 70 arranged on the housing 20 for controlling the water-pumping motor 120. In this embodiment, the housing 20 is opened and provided with a mounting hole. The key switch 70 is arranged in the mounting hole for controlling startup or shutdown of the water-pumping motor 120, thereby controlling spraying or shutdown of water of the aurilave. This making it convenient for the user to use, and effectively improves the practicality of the aurilave.

Further, as shown in FIGS. 1 to 5, the housing 20 is L-shaped. In this embodiment, the housing 20 has two functions. One function is that the user needs to hold the housing 20, and the other function is that the housing 20 needs to be mounted with the ear-washing assembly for water spraying and cleaning. In this embodiment, the housing 20 is arranged as an L-shape so that the user can easily hold the housing 20, and that a height of a space of the aurilave is effectively reduced to make it more user-friendly.

Further, as shown in FIGS. 1 to 5, the ear-washing assembly further includes a battery 80. The battery 80 is arranged within the housing 20 and electrically connected to the control plate 110. In this embodiment, the battery 80 is configured to supply power to the water-pumping motor 120 and the LED lamp plate 180. Specifically, the battery 80 is arranged in the housing 20, is electrically connected to the control plate 110, and stably supplies power to the water-pumping motor 120 and the LED lamp plate 180 via the control plate 110.

Further, as shown in FIGS. 1 to 5, the ear-washing assembly further includes a gravity ball 190 arranged at one end of the water inlet pipe 130 extending into the water storage tank 10. In this embodiment, since the water inlet pipe 130 is generally a hose, when immersed in a liquid, the water inlet pipe floats on a surface of the liquid due to a buoyant force of the liquid, thereby affecting pumping efficiency of the water-pumping motor 120. Therefore, in this embodiment, one end of the water inlet pipe 130 extending into the water storage tank 10 is provided with the gravity ball 190, thereby effectively maintaining a water inlet end of the water inlet pipe 130 at a bottom of the water storage tank 10. This further maintains the pumping efficiency of the water-pumping motor 120, and effectively improves the practicality of the aurilave.

Figure 3:
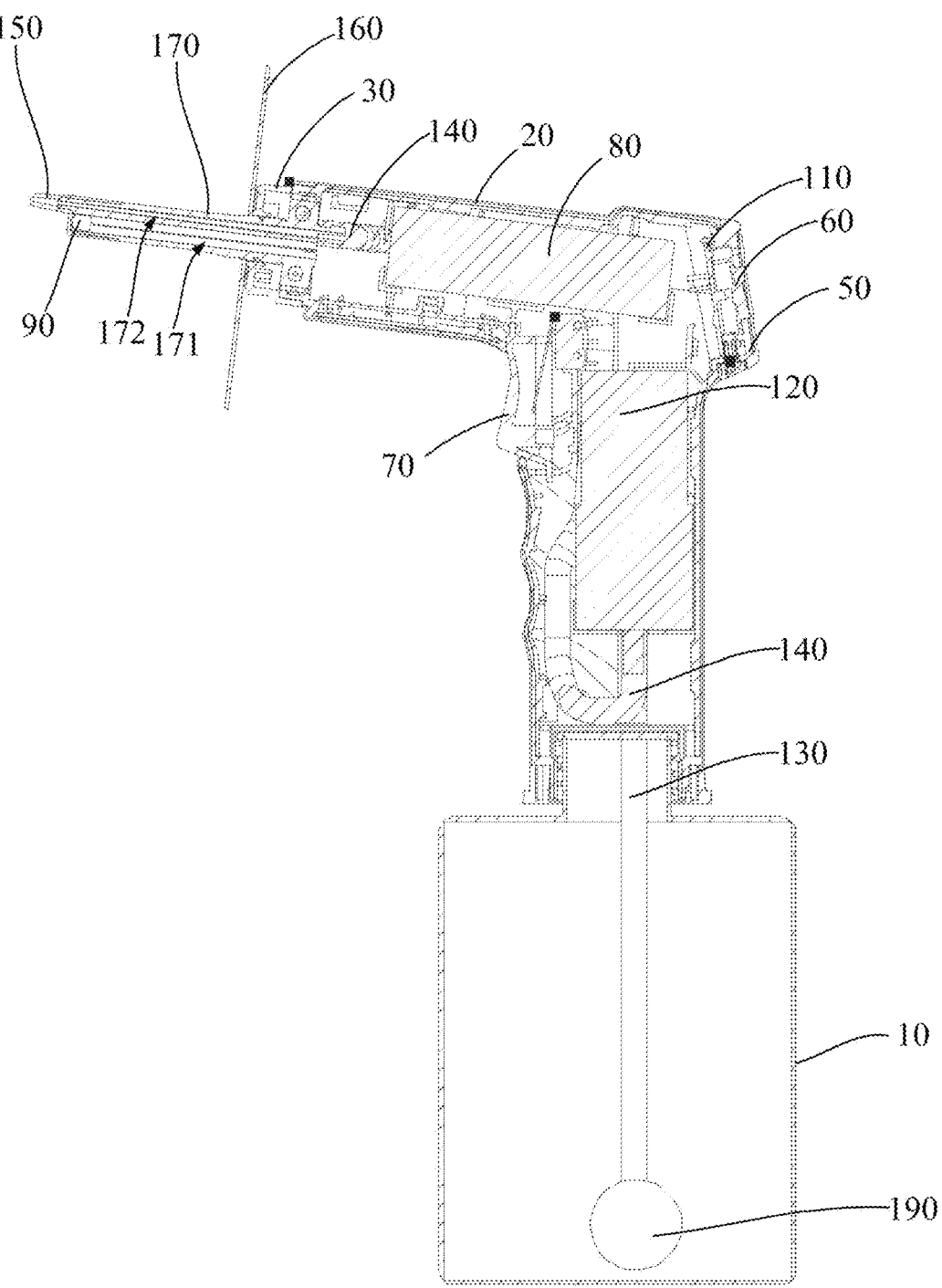
FIG. 3 is a cross-sectional schematic diagram of a visual aurilave according to the present invention.
Figure 4:
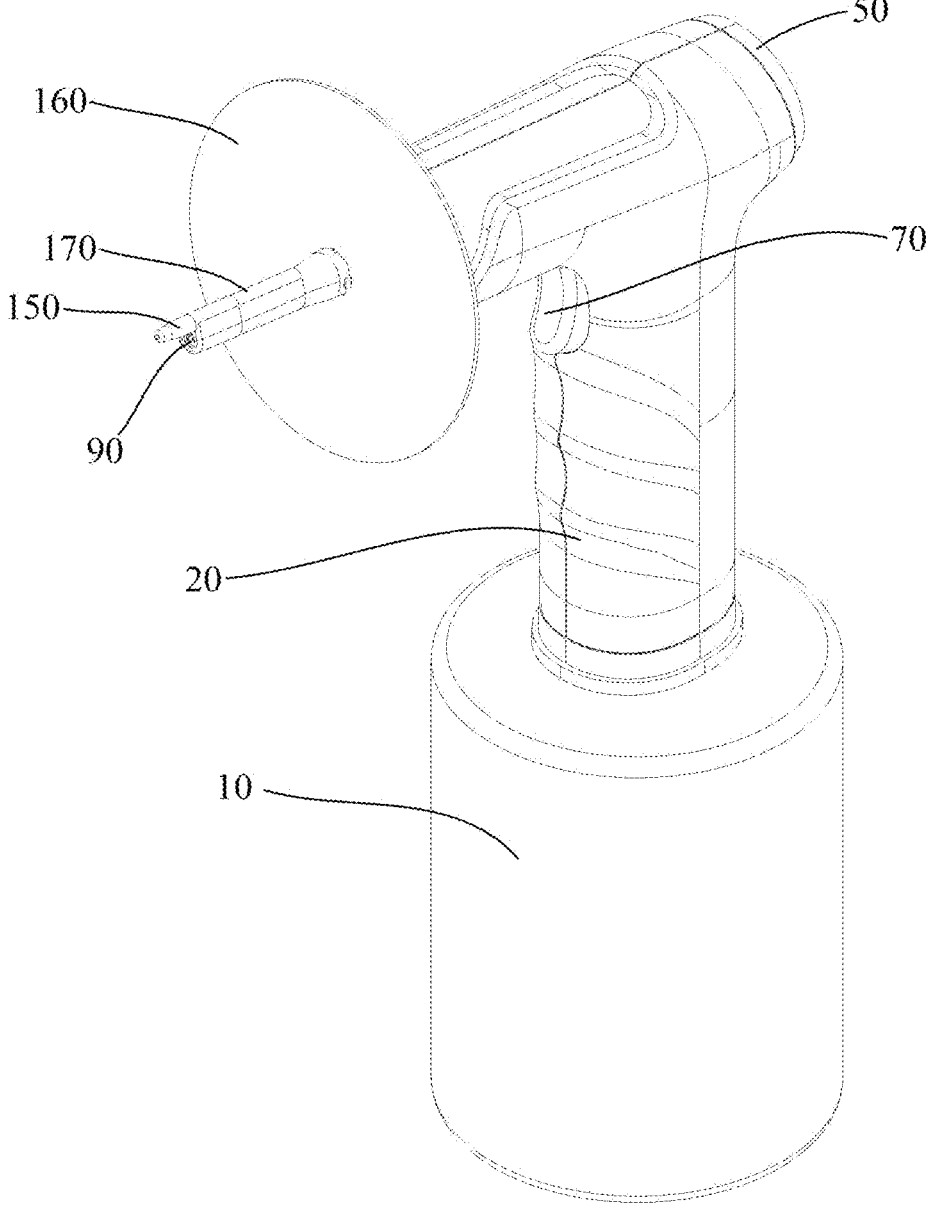
FIG. 4 is a schematic structural diagram of a visual aurilave according to the present invention.
Figure 5:
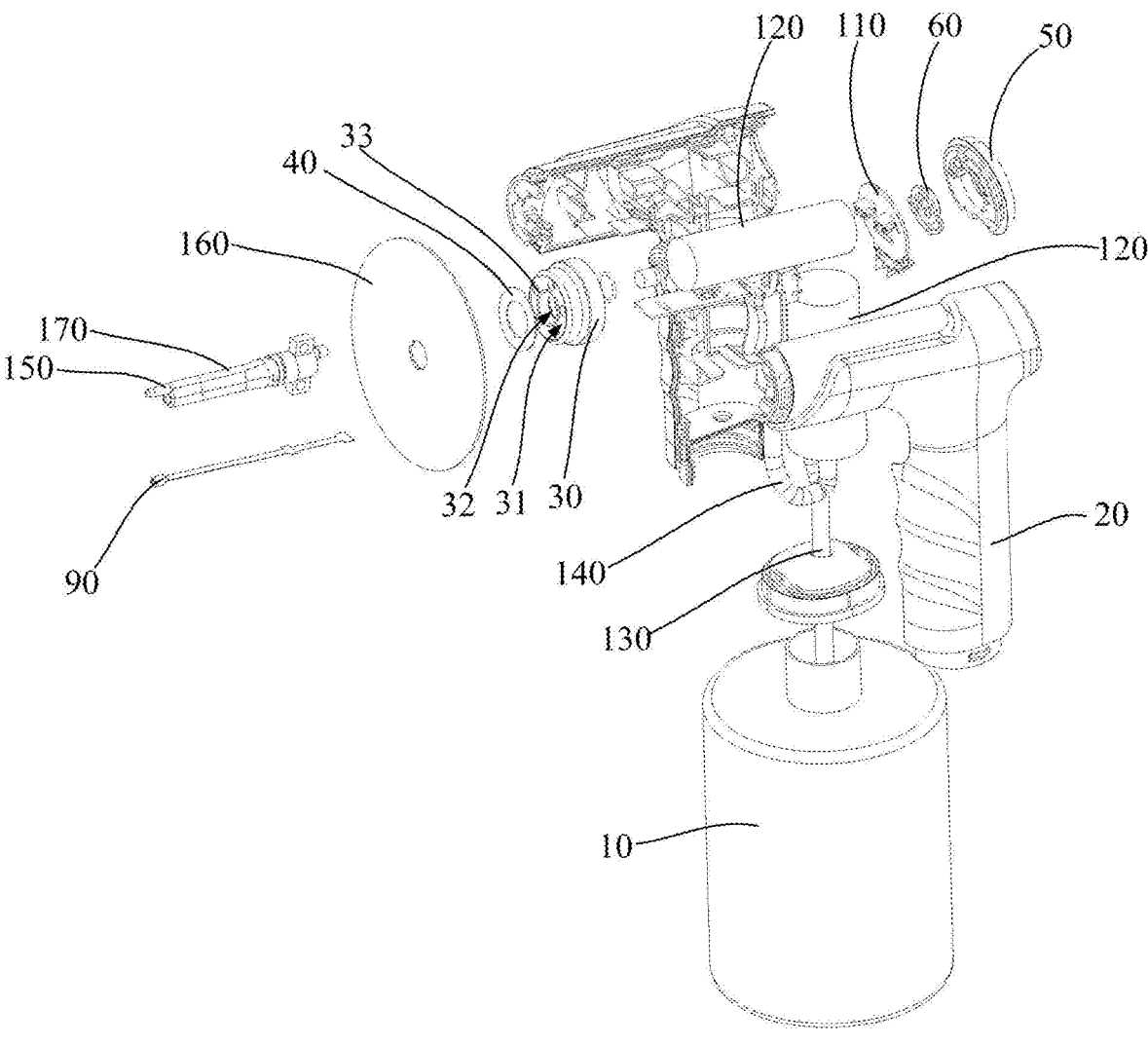
FIG. 5 is a schematic structural exploded diagram of a visual aurilave according to the present invention.

The present invention also proposes a visual aurilave. As shown in FIGS. 3 to 5, the visual aurilave includes: a water storage tank 10 provided with a mounting port;

a housing 20 detachably arranged on the mounting port of the water storage tank 10;

an ear-washing assembly including a control plate 110 arranged in the housing 20, a water-pumping motor 120 arranged in the housing 20 and electrically connected to the control plate 110, a water inlet pipe 130 connected to a water inlet port of the water-pumping motor 120 at one end thereof, a water outlet pipe 140 connected to a water outlet port of the water-pumping motor 120 at one end thereof, a nozzle 150 arranged on the other end of the water outlet pipe 140, and a transparent water baffle 160 arranged on the water outlet pipe 140. The other end of the water inlet pipe 130 extends into the water storage tank 10, and a camera assembly 90 including a camera 91 arranged on the ear-washing assembly and a signal-transmitting module arranged on the control plate 110. The camera 91 is electrically connected to the control plate 110 and arranged close to the nozzle 150. The signal-transmitting module is configured to transmit video signals captured by the camera 91 to a display apparatus.

It is to be explained that specific structures of the water storage tank 10, the housing 20, and the ear-washing assembly of the visual aurilave are the same as features of the corresponding embodiments of the aurilave described above, and thus are not repeated.

The camera assembly 90 is used for the user to observe the situation in the ear canal. Specifically, the camera 91 is arranged on the ear-washing assembly and close to a nozzle 150. Additionally, a signal-transmitting module is arranged on a control plate 110. The camera 91 shoots a video image in the ear canal to form video signals and transmits the video signals to the control plate 110. The control plate 110 transmits the video signals to a display apparatus for display via the signal-transmitting module, so that the user can view cleaning conditions of various corners in the ear canal in real time on the display apparatus, thereby making it more convenient for the user to clean the ear canal.

A transmission mode of the signal-transmitting module can be wired transmission or wireless transmission, which are not limited specifically here.

Further, the sprinkler seat 170 is opened and provided with a mounting channel 171. The camera 91 is arranged within the mounting channel 171 to prevent the camera from being eroded by a cleaning liquid. The mounting channel 17 is specifically arranged below the water guiding channel 172. It needs to be explained that the mounting channel 171 is arranged parallel to the water guiding channel 172. The mounting channel 171 has a length less than that of the water guiding channel 172. The camera is arranged at one end of the mounting channel 171 close to the nozzle 150, so that the user can observe a cleaning condition of the ear canal flushed by the nozzle 150. Therefore, the user can adjust a cleaning position according to the cleaning condition at any time, thereby effectively improving cleaning efficiency of the aurilave.

Figure 6:
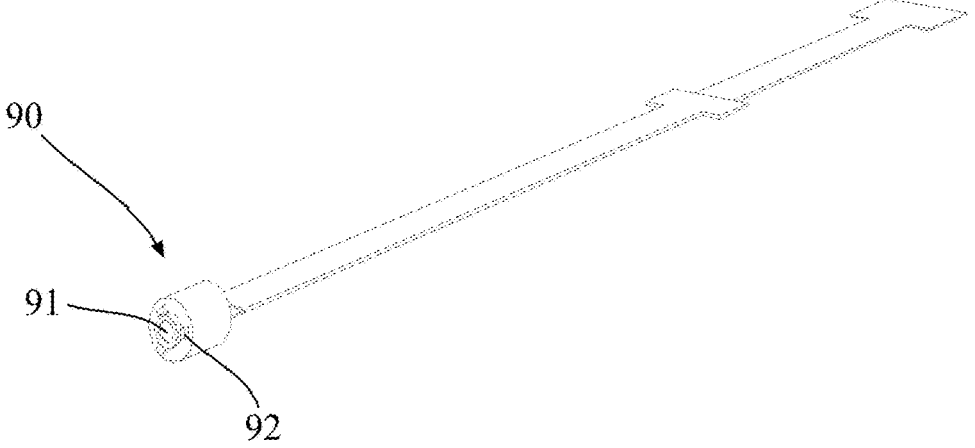
FIG. 6 is a schematic structural diagram of a camera assembly of a visual aurilave according to the present invention.

Further, as shown in FIG. 6, the camera assembly 90 further includes a plurality of LED lamp beads 92 arranged on the camera 91. The LED lamp beads 92 are provided on the camera 91 and arranged in a circular shape.

The forgoing is only a preferable embodiment of the present invention, and is not intended to limit the patent scope of the present invention. Under the inventive concept of the present invention, an equivalent structure variation made by the contents of the description and drawings of the present invention directly or indirectly applied to other related arts is included in the scope of patent protection of the present invention.

What is claimed is:

1. An aurilave, comprising:

a water storage tank provided with a mounting port;

a housing detachably arranged on the mounting port of the water storage tank; and, an ear-washing assembly comprising a control plate arranged in the housing, a water-pumping motor arranged in the housing and electrically connected to the control plate, a water inlet pipe connected to a water inlet port of the water-pumping motor at one end thereof, a water outlet pipe connected to a water outlet port of the water-pumping motor at one end thereof, a nozzle arranged on the other end of the water outlet pipe, and a transparent water baffle arranged on the water outlet pipe, the other end of the water inlet pipe extending into the water storage tank;

wherein the ear-washing assembly comprises a sprinkler seat, one end of the sprinkler seat is fixed in the housing and communicated with the water outlet pipe, and the other end of the sprinkler seat extends out of the housing, and the nozzle is arranged at one end of the sprinkler seat located outside the housing;

the ear-washing assembly further comprises a front cover arranged on the housing and an LED lamp plate arranged within the front cover and emitting light in a direction toward the nozzle, a middle of the front cover is opened and provided with a fixing hole for fixing the sprinkler seat, and the front cover is opened and provided with a light-transmitting hole for accommodating lamp beads of the LED lamp plate.

2. The aurilave according to claim 1, wherein the front cover is formed with a sealing groove relative to the other side of the LED lamp plate, the light-transmitting hole is located at a bottom of the sealing groove, and the aurilave further comprises a transparent sealing ring arranged in the sealing groove.

3. The aurilave according to claim 1, wherein the transparent water baffle is in a form of a disk raised in a middle thereof.

4. The aurilave according to claim 1, wherein the ear-washing assembly further comprises a rear cover and a power switch arranged on the rear cover, and the power switch is electrically connected to the control plate.

5. The aurilave according to claim 1, wherein the ear-washing assembly further comprises a key switch arranged on the housing for controlling the water-pumping motor.

6. The aurilave according to claim 1, wherein the housing is L-shaped.

7. The aurilave according to claim 1, wherein the ear-washing assembly further comprises a battery, and the battery is arranged within the housing and electrically connected to the control plate.

8. The aurilave according to claim 1, wherein the ear-washing assembly further comprises a gravity ball, and the gravity ball is arranged at one end of the water inlet pipe extending into the water storage tank.

9. A visual aurilave, comprising:

a water storage tank provided with a mounting port;

a housing detachably arranged on the mounting port of the water storage tank;

an ear-washing assembly comprising a control plate arranged in the housing, a water-pumping motor arranged in the housing and electrically connected to the control plate, a water inlet pipe connected to a water inlet port of the water-pumping motor at one end thereof, a water outlet pipe connected to a water outlet port of the water-pumping motor at one end thereof, a nozzle arranged on the other end of the water outlet pipe, and a transparent water baffle arranged on the water outlet pipe, the other end of the water inlet pipe extending into the water storage tank; and a camera assembly comprising a camera arranged on the ear-washing assembly and a signal-transmitting module arranged on the control plate, the camera being electrically connected to the control plate and arranged close to the nozzle, the signal-transmitting module being configured to transmit video signals captured by the camera to a display apparatus;

the ear-washing assembly comprises a sprinkler seat, one end of the sprinkler seat is fixed in the housing and communicated with the water outlet pipe, and the other end of the sprinkler seat protrudes out of the housing, and the nozzle is arranged at one end of the sprinkler seat located outside the housing;

the camera assembly further comprises a plurality of LED lamp beads provided on the camera and arranged in a circular shape;

the ear-washing assembly further comprises a front cover arranged on the housing and an LED lamp plate arranged within the front cover and emitting light in a direction toward the nozzle, a middle of the front cover is opened and provided with a fixing hole for fixing the sprinkler seat, and the front cover is opened and provided with a light-transmitting hole for accommodating the lamp beads of the LED lamp plate;

the front cover is formed with a sealing groove relative to the other side of the LED lamp plate, the light-transmitting hole is located at a bottom of the sealing groove, and the aurilave further comprises a transparent sealing ring arranged within the sealing groove.

10. The visual aurilave according to claim 9, wherein the sprinkler seat is opened and provided with a mounting channel, and the camera is arranged in the mounting channel.

11. The visual aurilave according to claim 9, wherein the transparent water baffle is in a form of a disk raised in a middle thereof.

12. The visual aurilave according to claim 9, wherein the ear-washing assembly further comprises a rear cover and a power switch arranged on the rear cover, and the power switch is electrically connected to the control plate.

13. The visual aurilave according to claim 9, wherein the ear-washing assembly further comprises a key switch arranged on the housing for controlling the water-pumping motor.

14. The visual aurilave according to claim 9, wherein the housing is L-shaped.

15. The visual aurilave according to claim 9, wherein the ear-washing assembly further comprises a gravity ball, and the gravity ball is arranged at one end of the water inlet pipe extending into the water storage tank.

5

\* \* \* \* \*